US007148036B2

(12) United States Patent
Luyten et al.

(10) Patent No.: US 7,148,036 B2
(45) Date of Patent: Dec. 12, 2006

(54) DNA MOLECULES ENCODING CARTILAGE-DERIVED MORPHOGENETIC PROTEINS

(75) Inventors: Frank P. Luyten, Rockville, MD (US); Malcolm Moos, Jr., Bethesda, MD (US); Steven Chao-Huan Chang, Chicago, IL (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/574,819

(22) Filed: May 19, 2000

(65) Prior Publication Data

US 2003/0185898 A1    Oct. 2, 2003

Related U.S. Application Data

(63) Continuation of application No. 08/836,081, filed as application No. PCT/US94/12814 on Nov. 7, 1994, now abandoned.

(51) Int. Cl.
*C12P 21/00* (2006.01)
*C12N 1/21* (2006.01)
*C12N 5/10* (2006.01)
*C12N 15/00* (2006.01)
*C07H 21/04* (2006.01)
*C07K 14/51* (2006.01)

(52) U.S. Cl. ............... 435/69.1; 435/252.3; 435/320.1; 435/325; 536/23.5; 530/325

(58) Field of Classification Search ............... 435/69.1, 435/325, 252.3, 320.1; 530/350, 324; 536/23.5
See application file for complete search history.

(56) References Cited

U.S. PATENT DOCUMENTS

| 4,609,551 A | 9/1986 | Caplan et al. |
| 4,810,691 A | 3/1989 | Seyedin et al. |
| 4,935,497 A | 6/1990 | Veis et al. |
| 5,658,882 A | 8/1997 | Celeste et al. |
| 5,770,444 A | 6/1998 | Lee et al. |
| 5,801,014 A | 9/1998 | Lee et al. |
| 5,807,713 A | 9/1998 | Hotten et al. |
| 5,994,094 A | 11/1999 | Hotten et al. |
| 6,027,919 A * | 2/2000 | Celeste et al. ............. 435/69.7 |

FOREIGN PATENT DOCUMENTS

| WO | PCTEP93/00350 | 8/1993 |
| WO | PCT/US94/00657 | 7/1994 |
| WO | PCT/US94/07762 | 1/1995 |
| WO | PCT/EP94/02630 | 2/1995 |

OTHER PUBLICATIONS

Adamson, M.C., et la., "The mouse homolog of the Gibbon Ape Leukemia Virus Receptor: Genetic Mapping and a Possible Receptor Function in Rodents", Virology 183, 778-781 (1991).
Alberts, et al., "Molecular Biology of the Cell", Jan. 1994, Garland Publishing, Inc., New York, NY, p. 119.
Bowie, et al., Deciphering the message in protein sequences: tolerance to amino acid substitutions. Science, (Mar. 16, 1990), 247, (4948) pp. 1306-1310.
Chang, et al., "Cartilage-derived Morphogenetic Proteins", Journal of Biological Chemistry, vol. 269, No. 45, Issue of Nov. 11, pp. 28227-28234 1994.
Chomczynski, P., et al., "Single-Step Method of RNA Isolation by Acid Guanidinium Thiocyanate-Phenol-Chloroform Extraction", Analytical Biochemistry 162, 156-159, (1987).
Grimaldi, J.C., et al., "Geonomic Structure and Chromosomal Mapping of the Murine CD40 Gene", The Journal of Immunology 149, (12), 3921-3926, (1992).
Hötten, et al., Cloning and Expression of Recombinant Human Growth . . . , Biochemical and Biophysical Research Communications, vol. 204(2): 646-52, Oct. 28, 1994.
Invitrogen Product Catalog, 1995, p. 31.
Kingsley, D.M. "The TGF-βsuperfamily: new members, new receptors and new genetic tests of function in different organisms", Genes and Development, (Jan. 1994) 8 (2) 133-146.
Luyten, F.P., et al., "Purification and Partial Amino Acid Sequence of Osteogenin, a Protein Initiating Bone Differentiation", The Journal of Biological Chemistry 264 (23), 13377-13380, (1989).
Luyten, F.P., et al, "Recombinant Bone Morphogenetic Protein-4, Transforming Growth Factor β1, and Activin A enhance the Cartilage Phenotype of Articular Chonodrocytes in Vitro", Experimental Cell Res. 210, 224-229 (1994).
Lyons, K. M., et al., "Organogenesis and Pattern Formation in the Mouse: RNA Distribution Patterns Suggest a Role for Bone Morphogenetic Protein-2a (BMP-2A)", Development 109, 833-844 (1990).

(Continued)

*Primary Examiner*—David S. Romeo
(74) *Attorney, Agent, or Firm*—Knobbe, Martens, Olson & Bear, LLP

(57) ABSTRACT

The present invention is a purified cartilage extract that stimulates local cartilage formation when combined with a matrix and implanted into a mammal. This extract can conveniently be produced by a method which includes the steps of: obtaining cartilage tissue; homogenizing the cartilage tissue in the presence of chaotropic agents under conditions that permit separation of proteins from proteoglycans; separating the proteins from the proteoglycans and then obtaining the proteins. The step for separating the proteins from the proteoglycans can be carried out using a sepharose column. The extract can also be obtained by additionally including the steps of separating the proteins on a molecular sieve and then collecting the proteins having molecular weights in the 30 kDa to 60 kDa size range. Articular cartilage or epiphyseal cartilage can be used in the preparation of this purified extract.

6 Claims, 4 Drawing Sheets

OTHER PUBLICATIONS

Muthukumaran, N., et al., "Comparison of Bone Inductive Proteins of Rat an Porcine Bone Matrix", Biochemical and Biophysical Research Communications 131 (1), 37-41, (1985).

Ngo, et al., "The Protein folding Problem and Tertiary Structure Prediction", Merz and Le Grand (Eds), Aug. 1994, Springer Verlag, pp. 433-506 (Ch. 14).

Owens, E. M., et al., "Cell—Cell Interaction by Mouse Limb Cells During in Vitro Chondrogenesis, Analysis of the Brachpod Mutation$_1$", Developmental Biology 91, 376-388, (1982).

Paralkar, v. M. et al., "Affinity of Osteogenin, an Extracellular Bone Matrix Associated Protein Initialing Bone Differentiation, for Concanavalin A", Biochemical and Biophysical Research Communications 160(2), 419-424, (1989).

Pelton, R.W., et al., "Expression of Transforming Growth Factor β2 RNA during Murine Embryogenesis", Development 106, 759-767, (1989).

Ramachandran, G. N., et al., "Collagen and Cell Differentiation", Biochemistry of Collagen, Ch. 9, pp. 449-478, (1976).

Reddi, A. H., "Bone morphogenetic proteins: an unconventional approach to isolation of first mammalian morphogens", Cytokine and Growth Factor Reviews, 1997, vol. 8, No. 1, p. 11-20.

Sambrook, et al., "Molecular Cloning: A Laboratory Manual", 2$^{nd}$ edition, vol. 1, 2, & 3, Cold Spring Harbor Laboratory Press, Cold Spring Harbor, New York, U.S.A., Nov. 1989, p. 9.47-9.51, 11.4, 16.19 and 16.41-16.44.

Sampath, T.K., et al., "Isolation of Osteogenin, and extracellular matrix-associated, bone inductive protein, by Heparin Affinity Chomotography", Proc. Natl. Acad. Sci. USA 84, 7109-7113 (1987).

Scheerlinck, J. Y., et al., "Rredistribution of a Murine Humoral Immune Response Following Removal of an Immunodominant B cell epitope from a recombinant Fusion Protein." Molecular Immunology 30 (8), 733-739 (1993).

Shah, et al., "Neutralisation of TGF-β1 and TGF-β2 or exogenous addition of TGF-β3 to cutaneous rat wounds reduces scarring", Journal of Cell Science 108, 985-1002 (1995).

Siracusa, L. D., et al., "Mouse Chromosome 2", Mammalian Genome 4:S31-S46, (1993).

Sorgenate, N., et al., "Extractability of Lysozyme from Bovine Nasal Cartilage", Biochemica Biopysica Acta 284: 441-450, (1972).

Storm, E. E., et al., "Limb Alterations in Brachpodism Mice due to Mutations in a new Member of the TGF-β Superfamily", Nature 368: 639-643 (1994).

Storm, et al., Genbank Accession No. U08338, National Institutes of Health, Bethesda, Maryland, U.S.A., Jun. 6, 1994.

Vukicevic, et al., "Developing Human Lung and Kidney are Major sites for Synthesis of Bone Morphogenetic Protein-3 (Osteogenin)", The Journal of Hystochemistry and Cythochemistry 42(7): 869-875 (1994).

Vukicevic, et al., "Induction of nephrogenic mesenchyme by osteogenic protein 1 (bone morphogenetic protein 7)" Proc. Nat'l Acad Sci USA, Aug. 20, 1996; 93(17):9021-6.

Wozney, et al., "Novel Regulators of Bone Formation: Molecular Clones and Activities", Science 242, 1528-1534, see Table 1 at page 1531 (1988).

* cited by examiner

| | | | | | | | | | | |
|---|---|---|---|---|---|---|---|---|---|---|
| Xenopus CDMP-x | WI | I | APL | E | YEA | H | HCEG | V | C | D | FP LRSHLEPTNH A | (SEQ ID NO:16) |
| Human CDMP-1 | WI | I | APL | E | YEA | F | HCEG | L | C | E | FP LRSHLEPTNH A | (SEQ ID NO:17) |
| Chicken CDMP-x | WI | I | APL | E | YEA | Y | HCEG | D | C | E | FP LRSHLEPTNH A | (SEQ ID NO:18) |
| Zebrafish CDMP-3 | WI | V | APL | D | YEA | Y | HCEG | V | C | D | FP LRSHLEPTNH A | (SEQ ID NO:19) |
| Xenopus CDMP-x | WI | I | APL | E | YEA | Y | HCEG | V | C | D | FP LRSHLEPTNH A | (SEQ ID NO:20) |
| Human CDMP-2 | WI | I | APL | E | YEA | Y | HCEG | V | C | D | FP LRSHLEPTNH A | (SEQ ID NO:21) |
| Bovine CDMP-2 | WI | I | APL | E | YEA | Y | HCEG | V | C | D | FP LRSHLEPTNH A | (SEQ ID NO:22) |
| Zebrafish CDMP-x | WI | M | APL | D | YEA | Y | HCEG | D | C | D | FP LRSHLEPTNH A | (SEQ ID NO:23) |
| | | | | | | | | | | | | |
| Consensus | WI | I | APL | E | YEA | Y | HCEG | V | C | D | FP LRSHLEPTNH A | (SEQ ID NO:24) |

SUBSTITUTE        FIGURE 4

DNA MOLECULES ENCODING CARTILAGE-DERIVED MORPHOGENETIC PROTEINS

This application is a continuation of prior application Ser. No. 08/836,081 filed Jul. 28, 1997 now abandoned which claims priority under 35 U.S.C. § 371 to PCT/US94/12814 filed Nov. 7, 1994.

FIELD OF THE INVENTION

The present invention relates generally to the field of cartilage and bone development. More specifically, the invention relates to cartilage-derived morphogenetic proteins that stimulate development and repair of cartilage in vivo.

BACKGROUND OF THE INVENTION

Bone morphogenetic proteins (BMPs) are members of the TGF-β superfamily that can induce endochondral bone formation in adult animals. This superfamily includes a large group of structurally related signaling proteins that are secreted as dimers and then cleaved to result in biologically active carboxy terminal domains of the proteins. These bioactive proteins are characterized by 7 highly conserved cysteine residues. Interestingly, these proteins have different roles at various stages of embryogenesis and in adult animals. Recombinant BMPs are now available and have been shown to induce endochondral bone formation when assayed in vivo.

Indeed, the initial discovery of the BMPs was facilitated by such in vivo assays for cartilage and bone development. These assays were based on the observation that bone development could be initiated by subcutaneous or intramuscular implantation of compositions comprising an extract of demineralized bone and residual bone powder. The novel proteins identified in the extracts were termed "bone morphogenetic proteins." These proteins were subsequently classified as members of the TGF-β superfamily by virtue of amino acid sequence relatedness. Screening of genomic and cDNA libraries led to the isolation of polynucleotides encoding BMP-2, -3, -4, -5, -6 and -7.

One deficiency of the bone induction assay regards its inability to distinguish the physiological roles of different BMP family members. The cartilage and bone inducing activity of the BMPs is remarkable because the normal stages of endochondral bone formation that occur during ontogeny are recapitulated in the adult animal. These stages include mesenchymal condensation, cartilage and bone and bone marrow formation and eventual mineralization to produce mature bone.

Several observations suggest that BMPs have wide-ranging extraskeletal roles in development. First, localization studies in both human and mouse tissues have demonstrated high levels of mRNA expression and protein synthesis for various BMPs in kidney (BMPs -3, -4, -7), lung (BMPs -3, -4, -5, -6), small intestine (BMPs -3, -4, -7), heart (BMPs -2, -4, -6, limb bud (BMPs -2, -4, -5, -7) and teeth (BMPs -3, -4, -7). Second, several members of the family, including BMP-4 and -7, are key molecules in epithelial-mesenchymal interactions, for instance during odontogenesis. Third, BMP-2 and BMP-4 are involved in the signaling pathway that controls patterning in the developing chick limb and BMP-4 is a ventralizing factor in early Xenopus development. Fourth, Drosophila homologs of the BMPs, the decapentaplegic (dpp) and 60 A gene products, have the capacity to induce bone in mammals whereas human BMP-4 confers normal embryonic dorso-ventral patterning in Drosophila transformants defective in dpp expression. Thus, the BMPs are now appreciated as pleiotropic cytokines.

Interestingly, none of the known BMPs are strongly expressed in the chondroblasts and chondrocytes of the cartilage core of developing long bones. The hypertrophic chondrocytes, where both Vgr-1 (BMP-6, (Lyons et al., Development 109:833 (1990)) and OP-1 (BMP-7) (Vukicevic et al., Biochem. Biophys. Res. Commun. 198:693 (1994)) have been found are exceptions in this regard.

SUMMARY OF THE INVENTION

One aspect of the present invention is a purified cartilage extract that stimulates local cartilage formation when combined with a matrix and implanted into a mammal. This extract can conveniently be produced by a method which includes the steps of: obtaining cartilage tissue; homogenizing the cartilage tissue in the presence of chaotropic agents under conditions that permit separation of proteins from proteoglycans; separating the proteins from the proteoglycans and then obtaining the proteins. The step for separating the proteins from the proteoglycans can be carried out using a sepharose column. The extract can also be obtained by additionally including the steps of separating the proteins on a molecular sieve and then collecting the proteins having molecular weights in the 30 kDa to 60 kDa size range. Articular cartilage or epiphyseal cartilage can be used in the preparation of this purified extract.

A second aspect of the present invention is a method of preparing a partially purified articular cartilage extract having chondrogenic activity. This method includes the steps of first obtaining cartilage tissue; homogenizing the cartilage tissue in the presence of chaotropic agents under conditions that permit separation of proteins from proteoglycans; separating the proteins from the proteoglycans and finally obtaining the proteins. The separation of proteins and proteoglycans can be accomplished using a sepharose column. In particular, the step for separating proteins from proteoglycans can include isolating the proteins that bind heparin Sepharose in the presence of 0.15 M NaCl but not in the presence of 1 M NaCl. An additional step in the purification procedure can include separating the proteins on a molecular sieve and then obtaining the proteins having molecular weights between 30 kDa and 60 kDa.

A third aspect of the present invention is an isolated DNA molecule that encodes a protein having chondrogenic activity in vivo but substantially no osteogenic activity in vivo. More particularly, this aspect of the invention regards a molecule having a nucleotide sequence that can hybridize to a polynucleotide which has the nucleotide sequence SEQ ID NO:11 or SEQ ID NO:12 at 55° C. with 0.4×SSC and 0.1% SDS. The proteins encoded by such DNA molecles can have the amino acid sequences of SEQ ID NO:13 or SEQ ID NO:14.

A forth aspect of the present invention is a recombinant protein having chondrogenic activity in vivo but substantially no osteogenic activity in vivo. This protein can have the amino acid sequence of SEQ ID NO:13 or SEQ ID NO:14.

A fith aspect of the present invention is a method of stimulating cartilage formation in a mammal. This method includes the steps: supplying cartilage-derived morphogenetic proteins having in vivo chondrogenic activity; mixing the partially purified proteins with a matrix to produce a product that facilitates administration of that partially purified proteins and implanting this mixture into the body of mammal to stimulate cartilage formation at the site of implantation. The partially purified cartilage-derived morphogenetic proteins can be obtained from either articular cartilage or epiphyseal cartilage. The matrix can also include non-cellular material. Viable chondroblast or chondrocytes can also be included in the mixture prior to implantation. The mixture can be implanted either subcutaneously or intramuscularly.

A sixth aspect of the present invention is a composition that can be administered to a mammal for the purpose of stimulating chondrogenic activity at the site of administration without substantially stimulating osteogenic activity. This composition comprises at least one cartilage-derived morphogenetic protein and a matrix. The cartilage-derived morphogenetic protein can be derived from an extract of either articular cartilage or epiphyseal cartilage. In another embodiment, the cartilage-derived morphogenetic protein is a recombinant protein. This recombinant protein can have the amino acid sequence of either SEQ ID NO:13 or SEQ ID NO:14. The matrix used to create the composition can be either fibrin glue, freeze-dried cartilage, collagens or the guanidinium-insoluble collagenous residue of demineralized bone. Alternatively the matrix can be a non-resolvable matrix such as tetracalcium phosphate or hydroxyapatite.

BRIEF DESCRIPTION OF THE FIGURES

FIG. 1 presents the nucleotide (SEQ ID NO:11) and predicted amino acid sequence (SEQ ID NO:13) encoded by the full length human CDMP-1 cDNA.

FIG. 2 presents the nucleotide (SEQ ID NO: 12) and predicted amino acid sequence (SEQ ID NO:14) encoded by the bovine CDMP-2.

FIG. 4 shows an alignment of segments from predicted CDMP amino acid sequences in standard one letter code.

DETAILED DESCRIPTION OF THE INVENTION

Figure 3:
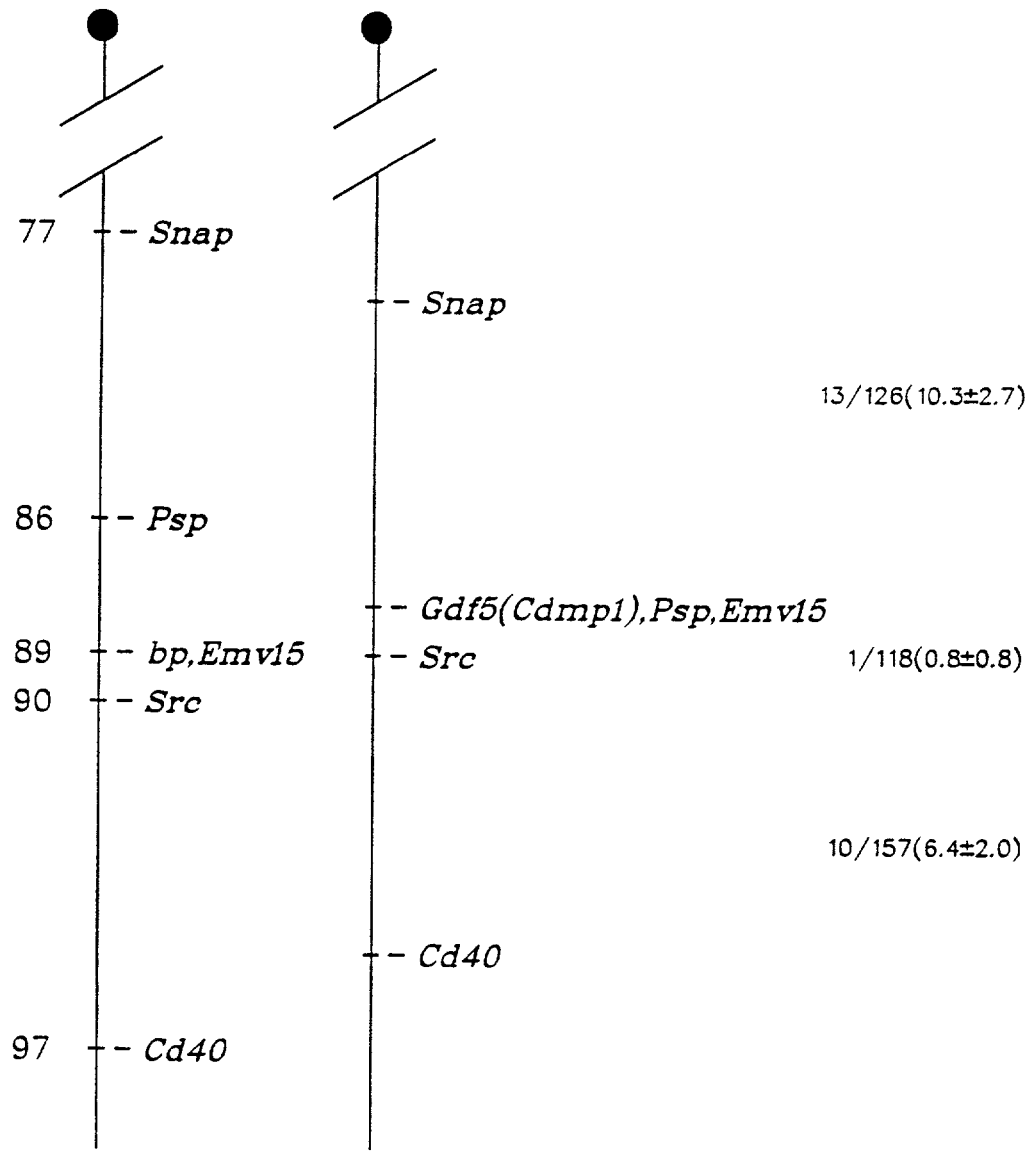
FIG. 3 presents the genetic maps of chromosome 2 showing the localization of CDMP-1. The map on the right is based on the data from two separate crosses.

We discovered that partially purified extracts of newborn calf articular cartilage contained an activity that induced cartilage formation when implanted subcutaneously in rats. This biological activity was reminiscent of that which characterized the BMPs. Degenerate oligonucleotide primer sets derived from the highly conserved carboxy-terminal region of the BMP family were employed in reverse transcription-polymerase chain reactions (RT-PCR) using poly(A)$^+$ RNA from articular cartilage as a template. These procedures allowed us to determine which BMPs were expressed in chondrocytes.

Two novel members of the TGF-β superfamily were identified and designated Cartilage-Derived Morphogenetic Protein-1 (CDMP-1), and -2 (CDMP-2). The C-terminal TGF-β domains of these proteins were 82% identical, thus defining a novel subfamily most closely related to BMP-5, BMP-6 and osteogenic protein-1. Northern analyses showed that postnatally both genes were predominantly expressed in cartilaginous tissues. In situ hybridization and immunostaining of sections from human embryos showed that CDMP-1 was predominantly found at the stage of precartilaginous mesenchymal condensation and throughout the cartilaginous cores of the developing long bones. CDMP-2 expression was restricted to the hypertrophic chondrocytes of ossifying long bone centers. Neither gene was detectable in the axial skeleton during human embryonic development. The cartilage-specific localization pattern of these novel TGF-β superfamily members, which contrasts with the more ubiquitous presence of other BMP family members, suggested a role for these proteins in chondrocyte differentiation and growth of long bones.

The discovery of a novel subfamily of cartilage derived morphogenetic proteins suggested the existence of morphogens that primarily functioned in the induction and maintenance (i.e., balancing cartilage and bone formation at articular surfaces) of cartilaginous and bony tissues. This subfamily may also include key molecules that govern bone marrow differentiation.

The cartilage-derived morphogenetic proteins contained in the cartilage extract of the present invention, and the recombinant CDMP-1 and CDMP-2 proteins described herein are contemplated for use in the therapeutic induction and maintenance of cartilage. For example, local injection of CDMPs as soluble agents is contemplated for the treatment of subglottic stenosis, tracheomalacia, chondromalacia patellae and osteoarthritic disease. Other contemplated utilities include healing of joint surface lesions (e.g. temporo-mandibular joint lesions or lesions induced posttraumatically or by osteochondritis) using biological delivery systems such as fibrin glue, freeze-dried cartilage grafts, and collagens mixed with CDMPs and locally applied to fill the lesion. Such mixtures can also be enriched with viable cartilage progenitor cells, chondroblasts or chondrocytes. We also contemplate repair or reconstruction of cartilaginous tissues using resolvable or non-resolvable matrices (tetracalcium phosphate, hydroxyapatite) or biodegradable polymers (PLG, polylactic acid/polyglycolic acid) coated or mixed with CDMPs. Such compositions may be used in maxilofacial and orthopedic reconstructive surgery. Finally, the CDMPs disclosed herein have utility as growth factors for cells of the chondrocyte lineage in vitro. Cells expanded ex vivo can be implanted into an individual at a site where chondrogenesis is desired.

We also anticipate the polynucleotides disclosed herein will also have utility as diagnostic reagents for detecting genetic abnormalities associated genes encoding CDMPs. Diagnostic testing could be performed prenatally using material obtained during amniocentesis. Any of several genetic screening procedures could be adapted for use with probes enabled by the present invention. These procedures include restriction fragment length polymorphism (RFLP), ligase chain reaction (LCR) or polymerase chain reaction (PCR).

We began our investigations by considering whether there were differences between the chondrogenic/osteogenic differentiation factors that characterized calcifying (epiphyseal, scapular cartilage) and non calcifying (articular, nasal septum) cartilage tissues. It had been previously established that tail tendon, achilles tendon, cartilage and skin matrices were devoid of chondrogenic/osteogenic activity (originally described as "transforming potency") as measured in an in vivo subcutaneous implantation model in rats (Reddi A. H., 1976, "Collagen and Cell differentiation" in *Biochemistry of Collagen*, eds. Ramachandran G. N. and Reddi, A. H., pp 449–478, Plenum Press, New York and London.).

We confirmed the absence of chondrogenic or osteogenic activity in crude 4 M guanidine HCl (GdnHCl) extracts of cartilage matrices, but unexpectedly discovered in vivo chondrogenic activity in the 0.15 M NaCl eluate of the cartilage extracts after ion exchange chromatography. The development of a unique extraction procedure (1.2 M Gdn- HCl and 0.5% CHAPs) followed by a heparin Sepharose affinity chromatography step confirmed the presence of in vivo chondrogenic activity in cartilaginous tissues. This was especially true in bovine articular and epiphyseal cartilage. When the bioactive heparin Sepharose eluates (1M NaCl eluate) were further purified using previously established procedures, molecular sieve chromatography and Con A affinity chromatography steps followed by SDS polyacrylamide gel electrophoresis and gel elution, chondrogenic activity was established. Implantation of 0.5 to 1 µg gel eluted material resulted in in vivo chondrogenesis. Surprisingly, and in contrast to the bone matrix purified activity, none of the peptide sequences that were found in tryptic digests of the highly purified cartilage extracts corresponded to any of the known BMPs. However, the biological activity present in the extracts was reminiscent of BMP-like activity by virtue of its loss of activity upon reduction and alkylation, its affinity for heparin Sepharose and Con A.

Although other materials and methods similar or equivalent to those described herein can be used in the practice or testing of the present invention, the preferred methods and materials are now described. General references for methods that can be used to perform the various nucleic acid manipulations and procedures described herein can be found in *Molecular Cloning: A Laboratory Manual* (Sambrook et al. eds. Cold Spring Harbor Lab Publ. 1989) and *Current Protocols in Molecular Biology* (Ausubel et al. eds., Greene Publishing Associates and Wiley-Interscience 1987). The disclosures contained in these references are hereby incorporated by reference. A description of the experiments and results that led to the creation of the present invention follows.

We initially discovered that an extract of cartilage possessed a unique chondrogenic activity. In particular, we discovered that newborn articular cartilage contained chondrogenic activities when assayed in the in vivo subcutaneous implantation model. Using a procedure adapted from that used for the isolation of BMPs from demineralized bone matrix, we partially purified this activity and thereby provided evidence for the presence of BMP-like molecules in cartilage.

Example 1 describes the biochemical methods used to characterize a chondrogenic activity present in bovine cartilage.

EXAMPLE 1

Characterization of Cartilage Derived Chondrogenic Activity

Articular (metatarsophalangeal joints), scapular and nasal cartilage (300 grams wet weight per tissue) were prepared from newborn calves. Epiphyseal cartilage was dissected from fetal bovine femurs (7–8 months). The tissues were finely minced and homogenized with a Polytron (top speed, 2×30 seconds) in 20 volumes of 1.2 M GdnHCl,0.5% CHAPS, 50 mM Tris-HCl pH 7.2, containing protease inhibitors and extracted overnight at 4° C. as described by Luyten et al., in *J. Biol. Chem.* 264:13377 (1989), which is hereby incorporated by reference. The disclosure of this article is hereby incorporated by reference. Sorgente et al., (*Biochem Biophys. Acta.* 282:441 (1972)) disclosed these procedures extract >90% of the lower molecular weight matrix while leaving most of the high molecular weight proteoglycans behind. The extracts were concentrated and exchanged with 6 M urea by diafiltration using an Ultrasette™ (Filtron Technology Inc., MA) and loaded on a 0.5 L heparin Sepharose (Pharnacia/LKB, NJ) column. Thereafter, the column was washed with 5 bed volumes of 6 M urea, Tris HCl pH 7.4 with 0.15 M NaCl, and then eluted with 2 vol 1 M NaCl in the same buffer. Chondrogenic activity was assayed by reconstituting a portion of the eluate with 25 mg of guanidine-insoluble collagenous residue of demineralized rat bone matrix according to procedures described by Luyten et al., in *J. Biol. Chem.* 264:13377 (1989). Implants were recovered after 10 days and alkaline phosphatase activity was measured as a biochemical indicator of cartilage and/or bone formation. The specific activity was expressed as units of alkaline phosphatase/mg of protein used for reconstitution in the bioassay. Implants were also examined histologically for evidence of cartilage formation using standard procedures known to those of ordinary skill in the art.

Additional purification steps were also performed. The 1 M NaCl eluate of articular cartilage, which contained biological activity, was concentrated by diafiltration and loaded onto a Sephacryl S-200 HR gel filtration column (XK 50/100, Pharmacia/LKB, NJ). After molecular sieve chromatography, the bioactive fractions were pooled and exchanged with 50 mM Hepes, pH 7.4, containing 0.15 M NaCl, 10 mM $MgSO_4$, 1 mM $CaCl_2$ and 0.1% (w/v) CHAPS using Macrosep™ concentrators (Filtron Technology Inc., Northborough, Mass.). The equilibrated sample was mixed with 1 ml Con A Sepharose (Pharmacia-LKB) previously washed with 20 volumes of the same buffer according to the procedure described by Paralkar et al., in *Biochem. Biophys. Res. Comm.* 131:37 (1989). After overnight incubation on an orbital shaker at 4° C., the slurry was packed into a disposable 0.7 cm ID Bio-Rad column and washed with 20 volumes of the Hepes buffer to remove unbound proteins. Bound proteins were eluted with 20 volumes of the same buffer containing 500 mM methyl-D-mannopyronaside. The eluate was concentrated to 200 µl using Macrosep™ concentrators. Macromolecules were then precipitated overnight with 9 volumes of absolute ethanol at 4° C. The precipitate was redissolved in 1 ml 6 M urea, Tris HCl pH 7.4. The bioactive bound protein was then mixed with 2× Laemmli sample buffer (without reducing agents) and electrophoresed on a 12% preparative SDS/polyacrylamide gel. Gel elution of the separated protein fractions and testing for biological activity was performed as described by Luyten et al., in *J. Biol. Chem.* 264:13377 (1989). We also observed that, after reduction with dithiothreitol and alkylation with iodoacetamide, substantially all of the cartilage-forming activity contained in the protein sample was lost.

Results indicated that each of the crude extracts of the different cartilaginous tissues (articular, nasal, scapular or epiphyseal) were inactive when tested directly in the in vivo cartilage and bone inducing assay. This finding confirmed previously described results published by Reddi in "Collagen and Cell differentiation" in *Biochemistry of Collagen* (eds. Ramachandran G. N. and Reddi, A. H., pp 449–478, Plenum Press, New York and London (1976)). However, after heparin affinity chromatography (Sampath et al., *Proc. Natl. Acad. Sci. U.S.A.* 84:7109 (1987)), chondrogenic activity was recovered in the 1 M NaCl eluate from articular cartilage extracts. An additional molecular sieve chromatography step (S200) was required to recover chondrogenic activity from epiphyseal cartilage extracts. Similar results were obtained upon ion exchange chromatography using DEAE Sephadex (0.15 M NaCl eluate). Significantly, no activity was detected in the extracts of the other cartilaginous tissues.

The highest specific activity was obtained for material derived from articular cartilage (1 U alkaline phosphatase/mg protein). This material was used for characterization of the bioactivity. Further purification of the active fraction by molecular sieve chromatography on Sephacryl S-200HR (specific activity 112 U/mg), and affinity chromatography on Concanavalin A (specific activity 480 U/mg), established the presence of cartilage and bone inducing activity characteristic of the members of the BMP family. Gel elution experiments with the Con A bound bioactive fraction demonstrated that the activity resided between roughly 34 and 38 kDa (specific activity of the gel eluted fractions was 2143 U/mg). We have also demonstrated that size separation by molecular sieve chromatography can be used to purify biological activity in the 30–60 kDa size range. In addition, loss of activity that was observed following reduction and alkylation suggested that the bioactivity was induced either by a known or a new member(s) of the BMP family.

Given the demonstration that cartilage contained a BMP-like activity, we proceeded to isolate polynucleotides encoding the responsible proteins. Specifically, degenerate primers corresponding to conserved regions of known BMPs were designed. These primers were then employed to amplify polynucleotides using reverse transcribed mRNA from articular cartilage as a template. These procedures ultimately led to the identification of two novel cDNAs, which we called CDMP-1 and CDMP-2.

Example 2 describes the methods used to amplify polynucleotides corresponding to mRNAs that were expressed in cartilage tissue and that exhibited at least weak sequence similarity to conserved regions of the BMP mRNAs.

EXAMPLE 2

PCR Amplification of cDNAs Encoding Cartilage-Derived Morphogenetic Proteins

Total RNA from bovine articular chondrocytes (metatarsophalangeal joints) was extracted using a modified acid guanidine-phenol-chloroform method described by Chomczynski et al., in *Anal. Biochem.* 162:156 (1987) and by Luyten et al., in *Exp. Cell. Res.* 210:224 (1994). Poly(A)$^+$ RNA was isolated using magnetic beads (PolyATract™, Promega, Madison, Wis.). Four degenerate oligonucleotide primers corresponding to highly conversed motifs in the C-terminal region of the BMPs were used; S1: 5'-GGITGG(C/A)AIGA(C/T)TGGAT(A/C/T)(A/G)TIGC(A/C/G/T)CC-3' (SEQ ID NO:1) corresponding to amino acids [GW(Q/N)DWI(I/V)AP] (SEQ ID NO:2); S2: 5'-GGITGG(A/T)(G/C)(I)GA(G/A)TGGAT(T/CA)ATI(A/T)G(A/C/G/T)CC-3' (SEQ ID NO:3) corresponding to amino acids [GWSEWIISP] (SEQ ID NO:4); AS1: 5'-A(A/G)(A/G)GT(C/T)TG(A/C/G/T)AC(A/G)AT(A/G)GC(A/G)TG(A/G)TT-3' (SEQ ID NO:5) corresponding to amino acids [NHAIVQTL] (SEQ ID NO:6); AS2:5'-CAI(C/G)C(A/G)CAI(G/C)(A/C/T)I(C/T)(C/G/T)IACIA(C/T)CAT-3' (SEQ ID NO:7) corresponding to amino acids [M(V/I)V(E/R)(G/S/A)C(G/A)C] (SEQ ID NO:8). Nucleotides in parenthesis denote sites of degeneracy and I denotes inosine. First strand cDNA synthesis was performed using 1 µg poly(A)$^+$ or 5 µg total RNA with oligo dT, random hexanucleotide primers, or the antisense degenerate primers, AS1 and AS2. Successful PCR amplifications were performed with the degenerate sense primers, S1 or S2 in combination with the AS1 antisense primer were performed using conditions described by Wharton et al., in *Proc. Natl. Acad. Sci. U.S.A.* 88:9214 (1991). The reaction products were electrophoresed on 1.2% agarose gels, and DNA fragments of appropriate sizes were excised and purified using the Magic PCR Prep DNA purification system (Promega, Madison, Wis.). Reamplification was performed with the same primers and each PCR product was subcloned into the PCR II vector using the TA Cloning™ System (InVitrogen Corporation, San Diego, Calif.). Results of RT-PCR using poly(A)$^+$ RNA isolated from newborn bovine articular cartilage as template and sets of degenerate oligonucleotide primers (S1/AS1 and S1/AS2) yielded amplification products of 120 bp and 280 bp.

Subcloned inserts were sequenced according to the dideoxy DNA sequencing method of Sanger et al., (*Proc. Natl. Acad. Sci. U.S.A.* 74:5463 (1977)). Both DNA strands were sequenced using Sequenase Version 2.0 DNA polymerase according to manufacturer's instructions (USB, Cleveland, Ohio) with at least two-fold redundancy. Confirmatory data in ambiguous regions were obtained by automated thermal cycle sequencing with an Applied Biosystems Model 370A sequencer and by using 7-deaza-GTP (USB, Cleveland, Ohio). The sequencing data were obtained from restriction fragments subcloned into pBluescript (Stratagene, La Jolla, Calif.) using either M13 forward and reverse primers or synthetic oligonucleotide primers.

The results from a computer-assisted search of the nucleic acid sequence databases indicated the cloned inserts encoded BMP-2, -6, BMP-7 (OP-1), and several other BMP-like sequences. Identification of these latter gene fragments led us to isolate larger cDNAs that included the entire protein coding region of the transcript. The availability of such clones facilitated both a more precise analysis of the encoded BMP-like protein and permitted studies aimed at localizing the expression of these genes. Thus, cloned inserts having novel BMP-like sequences were isolated, radiolabeled and used to screen both human and bovine articular cartilage cDNA libraries.

Example 3 describes the methods used to isolate human and bovine cDNAs that corresponded to a segment of one of the BMP-like gene segments that were amplified from cartilage mRNA templates.

EXAMPLE 3

Library Screening

Figure 1:
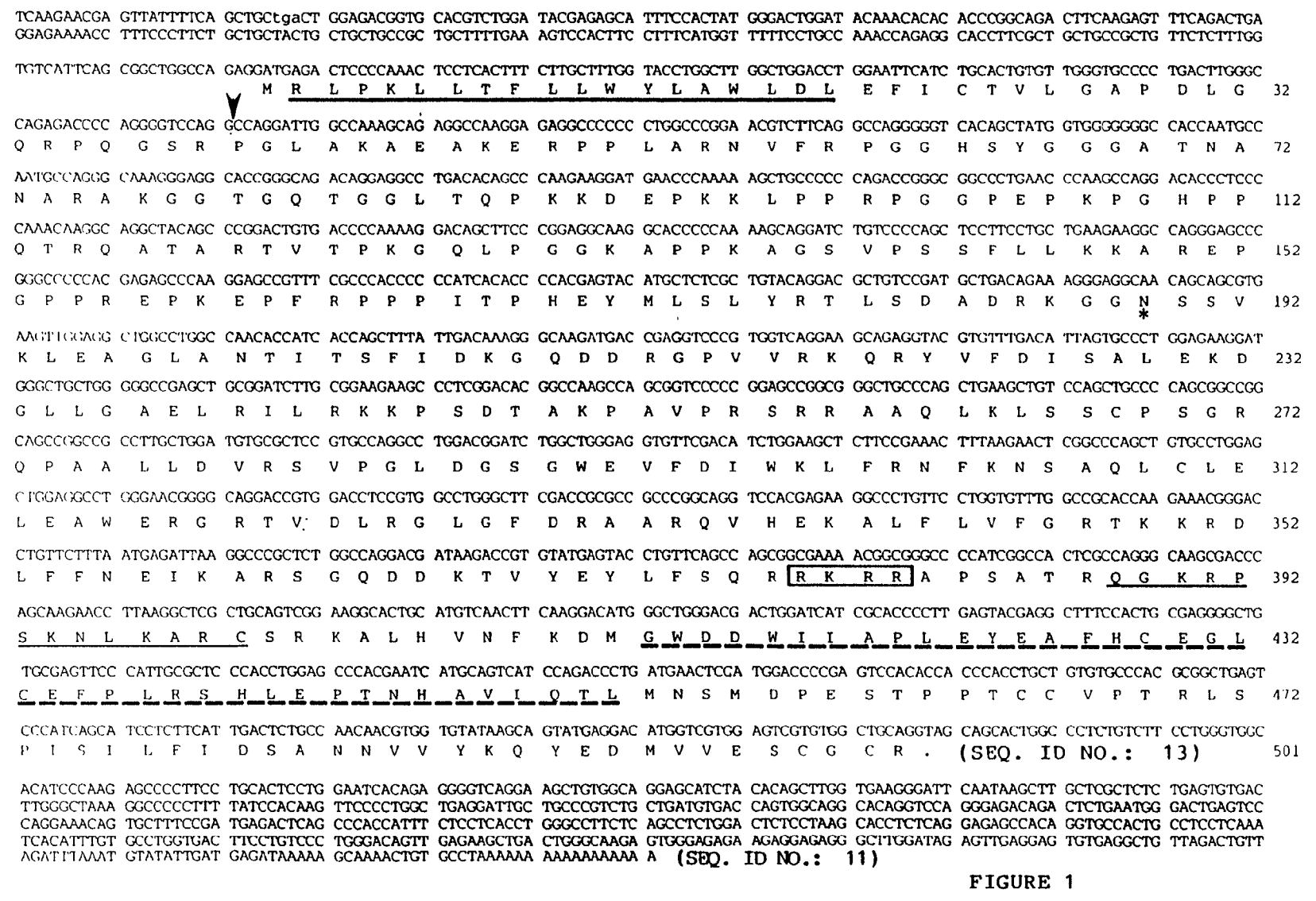

A 120 bp PCR fragment encoding part of the C-terminal domain of novel BMP like genes (dashed line, FIG. 1) was used to screen two cDNA libraries. One library, from adolescent human articular cartilage poly(A)$^+$ RNA (kindly provided by Dr. Björn Olsen, Harvard, Boston, Mass.), was primed with oligo dT and constructed in the λgt11 vector. The other was a bovine oligo dT and random primed articular cartilage cDNA library constructed in the UNIZAP®XR vector (Stratagene, La Jolla, Calif.). Approximately 1×10$^6$ plaques from each library were screened by standard procedures. Hybridizations were performed for 20 hours at 42° C. in 6×SSC, 1× Denhardt's solution, 0.01% tRNA, 0.05% sodium pyrophosphate and the membranes (DuPont 137 mm nylon membranes, New England Nuclear, MA) were washed to final stringency of 6×SSC, 0.1% SDS at 55° C. for 20 minutes.

Thus, cloned inserts having novel BMP-like sequences were isolated, radiolabeled and used to screen both human and bovine articular cartilage cDNA libraries. Six clones were isolated from the human cDNA library. The sizes of the EcoRI inserts (2.1 kb) and their restriction maps were found to be identical for all six clones. One clone was used for nucleotide sequencing. An open reading frame encoding a BMP related protein, designated CDMP-1, was identified. It appeared that the human cDNA clone lacked the coding region for the first methionine and signal peptide. The 5' end of the human CDMP-1 was subsequently obtained from a human genomic clone isolated from a library constructed in the EMBL-3 vector (Clontech, Palo Alto, Calif.). The 5' end of human CDMP-1 contained a consensus translation initiation sequence disclosed by Kozak (*J. Biol. Chem.* 266: 19867 (1991)) immediately followed by a putative transmembrane signal sequence described by Von Heijne (*Nucl. Acids Res.* 14:4683 (1986)). The nucleotide sequence and the translation of the open reading frame of CDMP-1 are presented in FIG. 1 and deposited at American Type Culture Collection (ATCC), 10801 University Blvd., Manassas, Va. 20110, USA, as PTA-2595, on Oct. 16, 2000. As shown in the figure, the CDMP-1 protein was predicted to have 500 amino acids, to consist of a pro-region of 376 amino acids, a typical cleavage site (Arg-Xaa-Xaa-Arg/Ala) (SEQ ID NO:9), and a C-terminal domain of 120 amino acids containing the seven highly conserved cysteines characteristic of the TGF-β gene family. A single N-linked glycosylation site is located in the pro-region (marked by an asterisk in the figure). A putative signal peptide is underlined in bold. A termination codon (TGA) is shown in the 5' untranslated region. The bold dashed underline indicates the fragment obtained by RT-PCR that was subsequently used to screen cDNA libraries. The 13 amino acid peptide used to raise polyclonal antibodies in rabbits is underlined. A vertical arrowhead marks the boundary between the sequence obtained from genomic DNA and cDNA.

Figure 2:
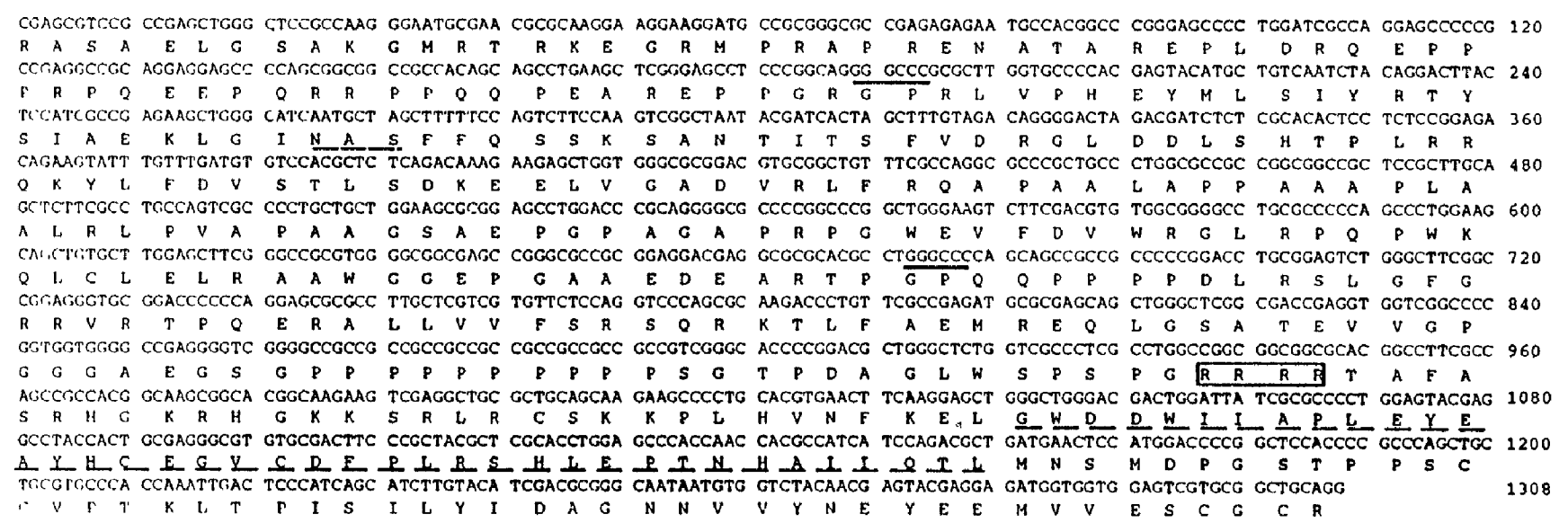

Two clones with inserts of 2.8 kb were isolated from a bovine articular cartilage cDNA library. Both clones were sequenced and the open reading frame was found to encode another novel TGF-β related protein, designated CDMP-2. The CDMP-2 cDNA and predicted protein sequences are presented in FIG. 2. As shown in the figure, the open reading frame contained a putative proteolytic processing site (boxed), preceding a 120 amino acid mature C-terminal region containing seven highly conserved cysteines. The 5' end with the first methionine and signal peptide were missing. The product obtained by RT-PCR (bold dashed underline) was used to screen a bovine cDNA articular cartilage library. The ApaI sites used to release a cDNA fragment for hybridization experiments are underlined. At the 5' end, the pro-region lacked the first methionine and signal peptide. The mature C-terminal domain of 120 amino acids showed 82% identity with CDMP-1.

Alignment of the carboxy terminal domains of CDMP-1 and -2 with other members of the BMP family revealed an amino acid identity of about 50% with BMP-5, BMP-6 and OP-1 (BMP-7). These results suggested that CDMP-1 and CDMP-2 are members of a new subfamily.

The amino acid sequence similarity between the human CDMP-1 and bovine CDMP-2 proteins prompted us to further investigate conservation of the CDMPs across different species. In particular, we employed a PCR amplification protocol to isolate CDMP cDNA sequences from a variety of species. Based on alignments of the predicted proteins encoded by these cDNAs, we identified a highly conserved amino acid sequence spanning 31 residues. Only 5 amino acid positions within this sequence showed variability. All remaining positions were identical for all isolates. As disclosed in the following Example, even the 5 variable positions showed a high degree of conservation. This structural conservation likely represents a functional domain that is characteristic of the CDMP family of proteins. Those of ordinary skill in the art will appreciate that such extraordinary amino acid sequence conservation is indicative of a functional domain. We therefore believe the consensus amino acid sequence presented in the following Example is critical to the biological activity of the CDMPs.

Example 4 describes the procedures used to identify an amino acid consensus sequence that characterizes the CDMPs from several different species.

EXAMPLE 4

Identification of a Highly Conserved Consensus Sequence in CDMP Proteins

RNA isolated from chicken sternal cartilage, bovine articular cartilage and human articular cartilage was employed as the template in RT-PCR protocols using the primers S1 and AS1 and procedures described under Example 2. Genomic DNA isolated from Xenopus and zebrafish was also used as the template for amplification of related gene sequences in a PCR protocol that employed the same primer sets. Amplified DNA fragments were subcloned according to standard procedures. The inserts from various isolates were sequenced by standard dideoxy chain termination protocols. Aligned segments of the predicted proteins encoded by the cloned cDNAs are presented in FIG. 4.

Results of the protein alignments clearly indicated that CDMP family members from several species shared a common amino acid sequence motif in the region of the proteins encoded by the amplified cDNA segments. Of the 31 amino acid positions presented in FIG. 4, all but 5 were occupied by identical amino acid residues for all of the isolates. The variable amino acids were located at positions 3, 7, 11, 16 and 18. Position 3 was occupied either by I, M or V. Position 7 was occupied by either D or E, both of which have acidic side groups. Position 11 was occupied by either Y, F or H. Position 16 was occupied by L or V, and position 18 was occupied by D or E. The consensus deduced from this alignment was: W-I-(I/M/V)-A-P-L-(D/E)-Y-E-A-(Y/F/H)-C-E-G-(L/V)-C-(D/E)-F-P-L-R-S-H-L-E-P-T-N-H-A (SEQ ID NO:15). This consensus sequence is slightly broader than the one shown in FIG. 4. as it encompasses all the variations observed in the sequenced polynucleotides. The consensus sequence in the figure indicates predominating amino acids.

We believe that biologically active CDMPs will possess this highly conserved amino acid sequence motif. Proteins having different amino acids in the variable positions in the consensus will likely represent novel family members having distinct functions. We also believe that polynucleotide hybridization probes or PCR primers designed based on this conserved protein motif can be used to isolate cDNAs encoding CDMP family members or related proteins.

Southern analyses were also carried out to investigate possible sequence conservation across species and to localize the CDMP-1 gene to a particular chromosome.

Example 5 describes the Southern blotting protocols used to detect DNA sequences corresponding to the CDMP-1 cDNA.

EXAMPLE 5

Genetic Mapping of CDMP-1

Southern hybridization was performed using the evolutionary relatedness blot (Bios Laboratories, New Haven, Conn.) under conditions recommended by the manufacturer. The panel of EcoRI-digested genomic DNAs included human (*homo sapiens*), mouse (*Mus musculus*), chicken (*Gallus domesticus*), frog (*Xenopus laevis*), lobster (*Homarus americanus*), mussel (*Mytilus edulis*), fish (*Tautoga onitis*), fruit fly (*Drosophila melanogaster*), nematode (*Caenorhabditis elegans*), yeast (*Saccharomyces cerevisiae*) and bacteria (*E. coli*). The 2.1 kb CDMP-1 EcoRI fragment originally obtained from the cDNA library was used as a probe, and the blot was washed to a final stringency of 0.4×SSC, 0.1% SDS, at 55° C.

Results from these Southern analyses using the original 2.1 kb human CDMP-1 cDNA probe (starting from amino acid position 40), showed 5.9 and 2.6 kb bands in humans and strong hybridization in both mouse and chicken. Fainter bands were seen in fish, frog and lobster after 5 days autoradiographic exposure. No hybridization was detected to *Drosophila* DNA.

The 2.1 kb ApaI fragment of CDMP-1 was used as a hybridization probe on Southern blots to type mouse genomic DNAs from two genetic crosses: (NFS/N or C58/J×*M. m. musculus*)×*M. m. musculus* (see Joseph et al., *Mol. Immunol.* 30:733 (1990)) and (NFS/N×*M. spretus*)×*M. spretus* or C58/J (see Adamson et al., *Virology* 183:778 (1991)). DNAs from these crosses have been typed for over 650 markers including the Chr 2 markers Snap (synaptosomal associated protein 25), Psp (parotid secretory protein), Emv15 (ecotropic murine leukemia virus 15), Src (src oncogene), and Cd40(cluster designation 40). Probes for these markers and restriction fragment length polymorphisms used to type these crosses have been described by Joseph et al., in *Mol. Immunol.* 30:733 (1990) and by Grimaldi et al., in *J. Immunol.* 149:3921 (1992). Src was typed using a mouse Src probe obtained from E. Rassart (U. Quebec, Montreal) following XbaI digestion in the *musculus* cross and BamHI digestion in the *spretus* cross.

Results from Southern blotting with the 2.1 kb cDNA described above identified EcoRI fragments of 7.1 and 2.0 kb in *M. spretus* and *M. m. musculus* and 6.8 and 3.2 kb in NFS/N and C58/J.

Inheritance of the polymorphic fragments in the progeny of the two crosses used for mapping was compared with inheritance of over 650 markers previously mapped to all 19 autosomes and the X chromosome. The gene encoding CDMP-1 was found to be linked to markers on Chr 2 just proximal to Src. The closest linkage was observed with Psp and Emv15. No recombination was observed between Cdmp1 and Psp in the 100 mice typed for both markers indicating that these genes are within 3.0 cM at the 95% confidence level. Similarly, the absence of recombination between Gdf5 (Storm et al., *Nature* 368:639 (1994)) and Cdmp1 in 125 mice suggested these genes colocalized within 2.4 cM. This map location suggested close proximity to the brachypodism locus (bp). A genetic map that presents the localization of CDMP-1 on chromosome 2 is shown in FIG. 3. Recombination fractions are given to the right of each map of the diagram for each adjacent locus pair or cluster. Numbers in parenthesis represent the percent recombination and standard error calculated as described by Green in *Genetics and Probability in Animal Breeding Experiments*, Oxford University Press, New York (1981). The map on the left is an abbreviated version of the Chr 2 Committee Map disclosed by Siracusa et al., in *Mammal Genome* 4:S31 (1993), and shows the map location of bp relative to the other markers typed in the crosses used here.

The brachypodism (bp mice) disorder is characterized by a distinct shortening of the limbs without other tissue abnormalities. The defect has previously been attributed to lack of production of a chondrogenic signal by mesenchymal cells at the time of chondrogenesis (Owens et al., *Dev. Biol.* 91:376 (1982)). During the course of our investigation, an independent study by Storm et al. (*Nature* 368:639 (1994)) described the isolation of the mouse CDMP-1 homolog, called Gdf-5, and established its linkage to the bracypodism (bp) mutation. The types of mutations observed in bp mice were found to be effective null-mutations for the gene encoding Gdf-5/CDMP-1. The pattern of expression of CDMP-1 throughout the cartilaginous core observed during human embryonic long bone development, coupled with the bp mutation in mice, indicated that its primary physiological role was most likely at the stage of early chondrogenesis and chondrocyte differentiation in the developing limb.

The foregoing results indicated the CDMP-1 and CDMP-2 cDNAs were novel, exhibited moderate sequence conservation across species as judged by evolutionary hybridization studies and that the CDMP-1 gene localized to mouse chromosome 2. We proceeded to examine the pattern of CDMP expression at the mRNA level.

Example 6 demonstrates the methods used to determine the pattern of CDMP mRNA expression.

EXAMPLE 6

CDMPs are Predominantly Expressed in Cartilage During Postnatal Life

Equal amounts of poly(A)$^+$ RNA (2 μg) from bovine criocoid and articular cartilage were electrophoresed on 1.2% agarose-formaldehyde gels and then transferred to Nytran membranes (Schleicher and Schuell, Kenne, N.H.) according to standard laboratory procedures. Multiple Tissue Northern blots were obtained from Clontech (Palo Alto, Calif.). The membranes were prehybridized for 3 hours at 42° C. in hybridization buffer (5×SSPE, 5×Denhardt's solution, 50% formamide, 1% SDS and 100 μg/ml freshly denatured salmon sperm DNA). Hybridizations with [$^{32}$P] dCTP labeled probes, having specific activities of at least 1×10$^9$ CPM/μg, were performed overnight under the same conditions as the prehybridization. Probes included the cDNA probe for human glyceraldehyde-3-phosphate dehydrogenase (1.1 kb, G3PDH (Clontech, Palo Alto, Calif.), an ApaI fragment (bp 470–1155) of CDMP-1, and an ApaI fragment (bp 194–677) of CDMP-2. The CDMP-1 and CDMP-2 probes were chosen to avoid the highly conserved carboxy-terminal domain, thereby minimizing the potential for cross hybridization with other members of the gene family. Following hybridization, the filters were washed to a final stringency of 55° C., 0.4×SSC, 0.1% SDS. The mRNA expression levels were quantified using a Phosphorimager (Molecular Dynamics, Sunnyvale, Calif.).

Results from Northern analyses of a number of postnatal tissues indicated that CDMP-1 could predominantly be detected in newborn articular and cricoid cartilage. In both cases a single mRNA transcript of approximately 3 kb was observed. The CDMP-1 mRNA was not detected in pancreas, kidney, skeletal muscle, liver, lung, placenta, brain or heart. In contrast, BMP-3 and BMP-7 transcripts were detected in subsequent hybridizations of the same blots in mRNA samples from lung, kidney, brain and small intestine. This finding was consistent with previous results disclosed by Vukicevic et al., (*J. Histochem. Cytochem.* 42:869 (1994)). CDMP-2 mRNA was detected in postnatal bovine articular and cricoid cartilage as a 4.6 kb mRNA band. After prolonged exposure, weak hybridization signals were detected at 4.6 kb and 4.0 kb in mRNA from colon and small intestine, skeletal muscle and placenta.

Two other procedures were used to localize and visualize expression of the CDMP-1 and CDMP-2 gene products. These approaches relied on detection of mRNA and protein in tissue sections prepared for analysis by microscopy.

Example 7 describes the methods used to demonstrate the preferential expression of CDMPs during human embryogenesis.

EXAMPLE 7

CDMPs are Preferentially Expressed in the Cartilaginous Cores of Long Bone During Human Embryogenesis In Situ Hybridization Tissues from human embryos were obtained after pregnancy termination at from 5 to 14 weeks of gestation. Embryo age was estimated in weeks (W) on the basis of crown-rump length (CRL) and pregnancy records of the conceptual age. They were fixed in 4% paraformaldehyde in 0.1 M phosphate buffer (pH 7.2), embedded in paraffin, sectioned serially at 5–7 µm, and mounted on silanated slides. The tissues used in the present study were obtained from legally sanctioned procedures performed at the University of Zagreb Medical School. The procedure for obtaining the human autopsy material was approved and controlled by the Internal Review Board of the Ethical Committee at the School of Medicine, University of Zagreb and Office of Human Subjects Research (OHSR) at the National Institutes of Health, Bethesda, Md. In situ hybridization was done as described by Vukicevic et al., (*J. Histochem. Cytochem.* 42:869 (1994)) and by Pelton et al. (*Development* 106:759 (1989)). Briefly, sections were incubated overnight at 50° C. in a humidified chamber in 50% formamide, 10% dextran sulfate, 4×SSC, 10 mM dithiothreitol, 1×Denhardt's solution, 500 µg/ml of freshly denatured salmon sperm DNA and yeast tRNA with 0.2–0.4 ng/ml $^{35}$S labeled riboprobe ($1\times10^9$ CPM/µg). ApaI fragments of CDMP-1 and of CDMP-2 (described above) from the pro region, subcloned in both sense and anti-sense direction into pBluescript II (SK)$^+$ vector (Strategene, CA), were used as transcription templates. Riboprobes were then prepared using T7 RNA polymerase (Sure Site Kit, Novagen, Madison, Wis.) according to the manufacturer's instructions and used with and without prior alkaline hydrolysis. After hybridization, the sections were washed as described by Lyons et al., in *Development* 109:833 (1990), to a final stringency of 0.1×SSC, 65° C. for 2×15 minutes. After dehydration through a graded ethanol series containing 0.3 M ammonium acetate, slides were covered with NTB-2 emulsion (Kodak) and exposed between 1 and 3 weeks. After development, the slides were stained with 0.1% toluidine blue, dehydrated, cleared with xylene and mounted with Permount.

Immunostaining

A polyclonal antibody to the peptide QGKRPSKN-LKARC (SEQ ID NO:10) (amino acids 388–400; prepared by Peptide Technologies, Gaithersburg, Md.), which belongs to the mature secreted protein of CDMP-1, was raised in rabbits. Before immunization, the peptide was conjugated to Imject$^R$ Malemide Activated Keyhole Limpet Hemocyanin (Pierce, Rockfor, Ill.). Searches performed using the BLAST (Altschul et al., *J. Mol. Biol.* 215:403 (1990)) network service available through the National Center for Biotechnology Information indicated that the peptide does not show sequence identity with any known protein or BMP. The embryonic tissue sections were stained as recommended by the manufacturer using immunogold as a detection system (Auroprobe LM; Janssen, Belgium) and counterstained with 0.1% toluidine blue. The primary antibody (crude antiserum) was used at a concentration of 15 µg/ml in PBS with 0.5% bovine serum albumin (BSA) for 1 hour. In the controls, the primary antibody was replaced with BSA, normal rabbit serum, or secondary antibody alone.

Results indicated that, at 6 weeks of gestation, CDMP-1 transcripts were detected in precartilage condensations within the developing limbs. At 7.5–8.5 weeks of gestation, CDMP-1 mRNA expression was found in the cartilaginous cores of long bones, including the articular surfaces. In areas of active cartilage degradation and bone matrix formation, CDMP-1 expression was also detected in hypertrophic chondrocytes. Remarkably, no expression was detected in the axial skeleton and only low mRNA levels were observed in other tissues, such as distal convoluted tubules of the developing kidney, brain and placenta. Immunohistochemical staining indicated that CDMP-1 protein colocalized with the mRNA. However, in addition to the sites of transcription, the protein was also found in the surrounding cartilaginous matrix and in osteoblast-like cells from the primary ossification centers of long bones.

Between 9 and 10 weeks of gestation, CDMP-2 expression was predominantly localized in the more mature and hypertrophic chondrocytes in regions of invasion by blood vessels through the periosteal bony collar of the developing long bone. Again, as for CDMP-1, no hybridization was detected in the vertebral bodies in the corresponding sections and stages of human embryonic development. Low expression levels were detected in the periosteum.

The expression pattern of CDMP-2 suggests it is involved in the terminal differentiation of chondrocytes (hypertrophic and mineralizing) and at the earliest stages of endochondral bone formation, including angiogenesis and osteoblast differentiation. In addition, the relatively high levels of expression (detectable in total RNA blots) in postnatal cartilage suggest possible roles in the maintenance and stabilization of the cartilage phenotype after birth.

We have also designed experiments aimed at determining whether all of the chondrogenic activity contained in cartilage extracts can be attributed to the proteins encoded by the CDMP-1 and CDMP-2 cDNAs. Our approach involves the production and use of neutralizing antibodies using synthetic peptides or recombinant CDMP-1 and CDMP-2 proteins as immunogens. Antibodies raised against these peptides or proteins will be tested for their ability to deplete cartilage extracts of chondrogenic activity. If antibodies specific for the recombinant proteins fail to deplete the extracts of cartilage-forming activity, then residual activity will be due to factors within the extract that are separate from proteins encoded by the CDMP-1 and CDMP-2 proteins. Alternatively, if antibodies raised against the peptides or recombinant proteins can remove cartilage-inducing activity from the extracts, this will confirm that CDMP-1 and/or CDMP-2 must be responsible for the active agents contained in the extracts.

Example 8 describes the methods that will be used to raise antibodies against synthetic peptides and recombinant CDMP-1 and CDMP-2 proteins. Antibodies produced in this fashion will be tested for their ability to deplete extracts containing CDMP activity.

EXAMPLE 8

Production and Use of Anti-CDMP Antibodies

Specific monoclonal and polyclonal antibodies will be raised against peptides designed from the mature protein of the CDMPs. Preferentially, the region between the protein cleavage site and the first cysteine of the CDMP-1 and CDMP-2 proteins will be used to design the peptides. In addition, the cDNAs encoding the mature region of the CDMPs will be subcloned in the bacterial pET expression vector, and expressed as monomers in the bacterial expression system. The protein expressed in this system will be used to raise additional antibodies, and to determine the immunoreactivity of the various antisera in Western blots. The bacterially expressed monomers will be refolded into biologically active dimers using standard protocols. This approach may afford another source of recombinant protein.

The antisera obtained in this fashion will be used to further establish the synthesis of the CDMPs by chondrocytes in vivo and in vitro, and to link the cloned CDMPs to the chondrogenic activity found in cartilage extracts. Conditioned media obtained from chondrocyte cultures and partially purified chondrogenic cartilage extracts after heparin sepharose affinity chromatography, molecular sieve chromatography and Con A chromatography, will be analyzed for the presence of CDMPs by Western blot analysis. Due to the possible heterogeneity of the highly purified chondrogenic cartilage extracts, the antibodies will be used to reduce or deplete the chondrogenic/osteogenic activity in purified fractions in a standard immunoprecipitation experiment.

An important aspect of our invention regards the production and use of recombinant proteins that possess the biological activities of the CDMPs. The following Example describes methods and results that illustrate the production of recombinant CDMP-1 and CDMP-2 in transfected 293 cells, COS-1 cells, and CHO-1 cells. We discovered that 293 cells express BMP-7 that could conceivably contaminate preparations of recombinant CDMPs. To avoid possible ambiguities in the interpretation of our results, recombinant CDMP-1 produced in COS-1 cells was used to demonstrate cartilage forming activity. Although the production of recombinant CDMPs in this fashion was rather inefficient, the key finding illustrated by our results was that recombinant protein had the desired cartilage-forming activity. Unexpectedly, and in contrast to the related BMPs, recombinant CDMP-1 induced cartilage formation without noticeable bone formation.

Example 9 describes the procedures used to produce recombinant CDMP proteins. The results presented in the Example confirm that the recombinant cartilage-derived proteins stimulated cartilage formation.

EXAMPLE 9

Production of Recombinant CDMPs and Assessment of Bioactivity

Full length CDMP-1 was subcloned into the mammalian expression vector pcDNA3 (Invitrogen Corporation, San Diego, Calif.) containing the cytomegalovirus early gene promotor and other elements required for expression in mammalian cells. COS 1 cells were cultured in Opti-MEM I (Gibco/BRL, Gaithersburg, Md.) in the presence of 5% fetal bovine serum and antibiotics. The cells were grown to approximately 70–80% confluency in 150 mm dishes and transfections of the respective plasmids (20 μg plamid) were carried out by the calcium phosphate method using the transfection MBS mammalian transfection kit (Stratagene, La Jolla, Calif.). The cells were incubated with the calcium phosphate-DNA mixture for 3 hours at 35° C. Supernatants were removed and the plates were washed 3 times with PBS. 15 ml of Opti-MEM I (serum reduced medium) was added in the absence of serum, and the dishes were incubated overnight. Transfection efficiencies were tested by transfection of a control plasmid, pCMVβ-gal and cell extracts were assayed for β-galactosidase activity. Conditioned media were collected at 24 hour intervals for a period of 96 hours. The pooled media was centrifuged to remove cell debris and then concentrated using Mascrosep 10 concentrators (Filtron Technology Inc., Northborough, Mass.). Further purification of recombinantly expressed protein was performed as described in preceding Examples. In one exemplary procedure, the conditioned media was adjusted to 4 M urea, 25 mM Tris HCl (pH 7.0) and applied to a heparin Sepharose column. The column was washed with the same buffer containing 0.1 M NaCl, and eluted with 1 M NaCl. The heparin Sepharose unbound and eluted fractions were assayed for biological activity as described by Luyten et al., in *J. Biol. Chem.* 264:13377 (1989).

Biological activity of the recombinantly expressed protein was investigated using in vitro and in vivo chondrogenic/osteogenic assays. For the in-vivo assay, fractions containing the CDMPs were precipitated with ethanol, or dried onto a carrier such as bone matrix residue (mainly collagen type I particles) and cartilage matrix residue (cartilage tissue after extraction with chaotropic agents, and powderized to particles with a size of 75–400 μm). The dried pellet (about 25 mg) was implanted subcutaneously in rats. Implants were harvested after 11 and 21 days, and analyzed for chondrogenesis/osteogenesis using alkaline phosphatase determinations. Histological analysis of recovered samples was also performed using toluidine blue, alcian blue and safranin O staining.

Results obtained using the recombinant CDMP-1 produced in COS-1 cells revealed chondrogenic activity in this in vivo assay. Significantly, no osteogenic activity was observed in any of the recovered samples. Osteogenic activity would ordinarily have been observed if the same procedures had been carried out using recombinant BMPs. This difference highlighted the unique properties of recombinant CDMP-1.

Future in vitro chondrogenic experiments will be performed to determine the precursor cells responsive to the CDMPs. Undifferentiated (10T1/2 cells, bone marrow stromal cells, mesenchymal stem cells) and already committed skeletal cells (limb bud cells, perichondrial or periosteal cells, fetal epihyseal chondroblasts, and chondrocytes) will be transfected with the cDNAs or treated with recombinantly expressed CDMPs to evaluate the stage of differentiation associated with the chondrogenic activity of the CDMPs.

Future in vivo chondrogenic experiments will be directed to expression of large quantities of CDMP-1 and CDMP-2 by stable transfectants. We contemplate the use of hybrid expression constructs in which the pro-region of one BMP family member (for example BMP-2) is operationally linked to the regions encoding the mature CDMPs. We also anticipate in vivo assays based on implantation in other sites, apart from subcutaneous implantation, which may reveal distinct or superior biological activities of the CDMPs. For example, we anticipate implantation in the synovial cavity may have utility in such assays.

The CDMPs disclosed in the present invention have important applications in the repair of cartilage defects. We contemplate two general approaches for this type of therapy. In the first place, the CDMPs are used as lineage-specific growth factors for the ex vivo expansion of chondrocytes isolated from a donor who requires therapeutic intervention. Following expansion, these cells can be reimplanted into a cartilage lesion in the donor, whereafter repair of cartilage will take place. In a different scenario, CDMPs are introduced into a cartilage lesion. For example, a composition containing an appropriate CDMP or mixture of CDMPs can be implanted into a lesion for the purpose of stimulating in viva chondrogenesis and repair of cartilage. The CDMPs can be combined with any of a number of suitable carriers. An appropriate carrier can be selected from the group comprising fibrin glue, cartilage grafts, and collagens. An implantable mixture can be introduced into the site of a lesion according to methods familiar to those having ordinary skill in the art. In one application, we contemplate that periosteal synovial membrane flap of tissue or inert material can be impregnated with CDMPs and implanted for cartilage repair.

Example 10 illustrates one application of the CDMP preparations described above. Specifically, the following Example describes the use of CDMPs to facilitate repair of cartilage in the knee joint.

EXAMPLE 10

Treatment of Deep Knee Defects with Cartilage-Derived Morphogenetic Proteins

A young patient having a large defect in the articular surface of the knee joint is identified. According to standard surgical procedures, a periosteal flap is obtained from the bone beneath the joint surface of rib cartilage. The tissue flap is pre-soaked in an extract containing CDMPs or alternatively in a solution containing recombinant CDMPs. The periosteal flap treated in this way is then attached over the lesion in the articular surface of the knee joint by a sewing procedure, for example using resolvable material. The joint is then closed. The joint is injected with a solution containing CDMPs dissolved or suspended in a pharmacologically acceptable carrier to maintain the chondrogenic process. Injection is continued until the monitoring physician indicates repair of the cartilage is complete. The patient notices markedly less joint pain as the cartilage repair process progresses. Exam by arthroscopy indicates repair of the lesion within several weeks following the initial procedure.

We also contemplate gene therapy protocols based on expression of CDMP cDNAs or genomic constructs as a way of facilitating in vivo cartilage repair. Diseases such as chondromalacia or osteoarthritis are examples for which such gene therapy protocols are contemplated. Therapy may be achieved by genetically altering synoviocytes, periosteal cells or chondrocytes by transfection or infection with recombinant constructs that direct expression of the CDMPs. Such altered cells can then be returned to the joint cavity. We contemplate that gene transfer can be accomplished by retroviral, adenoviral, herpesvirus and adeno associated virus vectors.

Both in vivo and ex vivo approaches are anticipated for continuously delivering CDMPs for the purpose of retarding ongoing osteoarthritic processes and for promoting cartilage repair and regeneration. In addition, one might employ inducible promoter constructs (e.g. under transcriptional control of a dexamethasone promoter) in gene therapy applications of the present invention. A combined approach to osteoarthritis therapy may have particular advantages. For example, CDMP-2 could be continuously expressed to support the integrity of the articular surface. An inducible construct could be employed to express CDMP-1 so that chondrogenesis could be accelerated at the time of more aggressive destruction.

The foregoing experimental results and characterization confirmed the CDMP-1 and CDMP-2 isolates belong to the TGF-β superfamily. Based on the high percentage identity of their C-terminal domains, CDMP-1 and CDMP-2 can be classified as members of a novel subfamily. Although CDMP-1 and CDMP-2 were identified in two different species (human and bovine), they represent distinct genes since the sequences of their pro-regions are significantly divergent.

Several BMPs have now been implicated in early skeletal development, including BMPs-2, -4, -5, -7 and CDMP-1 (GDF-5). Other members, such as BMPs-3, -6, -7 and CDMP-2, may be involved in later stages of skeletal formation (13, 15). The role of the BMPs in early development could be chemotactic, mitogenic or inductive. Their function in later stages of skeletal development might be promotion of differentiation and maintenance of the established phenotype. The availability of mouse strains with null mutations in specific BMP members, such as the short-ear mice (Bmp5) and the bp mice (Cdmp1/Gdf5), allows analysis of the specific contributions of the respective members in each of the stages of skeletal development.

The absence of expression of both CDMP-1 and CDMP-2 in the axial skeleton has implications for models of skeletal development. For example, the bp mice have disturbed limb development but a normal axial skeleton. This is the first evidence that the developmental mechanisms and differentiation pathways of the vertebral bodies are distinct from those of the peripheral skeletal elements. Further, this indicates the basic form and pattern of the skeleton are likely to be determined by a number of BMP-like signaling molecules.

We claim:

1. An isolated DNA molecule encoding the amino acid sequence of SEQ ID NO: 24.
2. An expression vector comprising the isolated DNA molecule of claim 1.
3. A host cell transformed with the vector of claim 2.
4. The host cell of claim 3 wherein said cell is eukaryotic.
5. The host cell of claim 4 wherein said cell is mammalian.
6. A process for the production of a protein comprising the amino acid sequence of SEQ ID NO: 24 comprising the steps of culturing the host cell of claim 3 in a culture media, and isolating the protein therefrom.

* * * * *

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 26 base pairs (B) TYPE: nucleic acid
        (C) STRANDEDNESS: single
        (D) TOPOLOGY: linear (ii) MOLECULE TYPE: cDNA (ix) FEATURE:
        (A) NAME/KEY: Other
        (B) LOCATION: 3...21
        (D) OTHER INFORMATION: inosine (xi) SEQUENCE DESCRIPTION: SEQ ID NO: 1:

GGNTGGMANG AYTGGATHRT NGCNCC                                              26

(2) INFORMATION FOR SEQ ID NO: 2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 3...3
        (D) OTHER INFORMATION: Xaa = Q or N (xi) SEQUENCE DESCRIPTION: SEQ ID NO: 2:

Gly Trp Xaa Asp Trp Ile Xaa Ala Pro
1               5

(2) INFORMATION FOR SEQ ID NO: 3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Other
        (B) LOCATION: 3...24
        (D) OTHER INFORMATION: inosine (xi) SEQUENCE DESCRIPTION: SEQ ID NO: 3:

GGNTGGWSNG ARTGGATHAT NWGNCC                                              26

(2) INFORMATION FOR SEQ ID NO: 4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Gly Trp Ser Glu Trp Ile Ile Ser Pro
1               5

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single (D) TOPOLOGY: linear (ii) MOLECULE TYPE: cDNA (ix) FEATURE:
            (A) NAME/KEY: Other
            (B) LOCATION: 9...9
            (D) OTHER INFORMATION: A or T or G or C (xi) SEQUENCE DESCRIPTION: SEQ ID NO: 5:

ARRGTYTGNA CRATRGCRTG RTT                                              23

(2) INFORMATION FOR SEQ ID NO: 6:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 6:

Asn His Ala Ile Val Gln Thr Leu
1               5

(2) INFORMATION FOR SEQ ID NO: 7:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: Other
            (B) LOCATION: 3...18
            (D) OTHER INFORMATION: inosine (xi) SEQUENCE DESCRIPTION: SEQ ID NO: 7:

CANSCRCANS HNYBNACNAY CAT                                              23

(2) INFORMATION FOR SEQ ID NO: 8:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 2...2
            (D) OTHER INFORMATION: Xaa = V or I (xi) SEQUENCE DESCRIPTION: SEQ ID NO: 8:

Met Xaa Val Xaa Xaa Cys Xaa Cys
1               5

(2) INFORMATION FOR SEQ ID NO: 9:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (ix) FEATURE:
           (A) NAME/KEY: Other
           (B) LOCATION: 2...2
           (D) OTHER INFORMATION: Xaa = any aa (xi) SEQUENCE DESCRIPTION: SEQ ID NO: 9:

Arg Xaa Xaa Xaa
 1

(2) INFORMATION FOR SEQ ID NO: 10:

(i) SEQUENCE CHARACTERISTICS:
           (A) LENGTH: 13 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 10:

Gln Gly Lys Arg Pro Ser Lys Asn Leu Lys Ala Arg Cys
 1               5                  10

(2) INFORMATION FOR SEQ ID NO: 11:

(i) SEQUENCE CHARACTERISTICS:
           (A) LENGTH: 2341 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 11:

| | | | | | |
|---|---|---|---|---|---|
| TCAAGAACGA | GTTATTTTCA | GCTGCTGACT | GGAGACGGTG | CACGTCTGGA | TACGAGAGCA | 60 |
| TTTCCACTAT | GGGACTGGAT | ACAAACACAC | ACCCGGCAGA | CTTCAAGAGT | TTCAGACTGA | 120 |
| GGAGAAAACC | TTTCCCTTCT | GCTGCTACTG | CTGCTGCCGC | TGCTTTTGAA | AGTCCACTTC | 180 |
| CTTTCATGGT | TTTTCCTGCC | AAACCAGAGG | CACCTTCGCT | GCTGCCGCTG | TTCTCTTTGG | 240 |
| TGTCATTCAG | CGGCTGGCCA | GAGGATGAGA | CTCCCCAAAC | TCCTCACTTT | CTTGCTTTGG | 300 |
| TACCTGGCTT | GGCTGGACCT | GGAATTCATC | TGCACTGTGT | TGGGTGCCCC | TGACTTGGGC | 360 |
| CAGAGACCCC | AGGGGTCCAG | GCCAGGATTG | GCCAAAGCAG | AGGCCAAGGA | GAGGCCCCCC | 420 |
| CTGGCCCGGA | ACGTCTTCAG | GCCAGGGGGT | CACAGCTATG | GTGGGGGGGC | CACCAATGCC | 480 |
| AATGCCAGGG | CAAAGGGAGG | CACCGGGCAG | ACAGGAGGCC | TGACACAGCC | AAGAAGGAT | 540 |
| GAACCCAAAA | AGCTGCCCCC | CAGACCGGGC | GGCCCTGAAC | CCAAGCCAGG | ACACCCTCCC | 600 |
| CAAACAAGGC | AGGCTACAGC | CCGGACTGTG | ACCCCAAAAG | GACAGCTTCC | CGGAGGCAAG | 660 |
| GCACCCCCAA | AAGCAGGATC | TGTCCCCAGC | TCCTTCCTGC | TGAAGAAGGC | CAGGGAGCCC | 720 |
| GGGCCCCCAC | GAGAGCCCAA | GGAGCCGTTT | CGCCCACCCC | CCATCACACC | CCACGAGTAC | 780 |
| ATGCTCTCGC | TGTACAGGAC | GCTGTCCGAT | GCTGACAGAA | AGGGAGGCAA | CAGCAGCGTG | 840 |
| AAGTTGGAGG | CTGGCCTGGC | CAACACCATC | ACCAGCTTTA | TTGACAAAGG | GCAAGATGAC | 900 |
| CGAGGTCCCG | TGGTCAGGAA | GCAGAGGTAC | GTGTTTGACA | TTAGTGCCCT | GGAGAAGGAT | 960 |
| GGGCTGCTGG | GGGCCGAGCT | GCGGATCTTG | CGGAAGAAGC | CCTCGGACAC | GGCCAAGCCA | 1020 |
| GCGGTCCCCC | GGAGCCGGCG | GGCTGCCCAG | CTGAAGCTGT | CCAGCTGCCC | CAGCGGCCGG | 1080 |
| CAGCCGGCCG | CCTTGCTGGA | TGTGCGCTCC | GTGCCAGGCC | TGGACGGATC | TGGCTGGGAG | 1140 |

```
GTGTTCGACA TCTGGAAGCT CTTCCGAAAC TTTAAGAACT CGGCCCAGCT GTGCCTGGAG   1200

CTGGAGGCCT GGGAACGGGG CAGGACCGTG GACCTCCGTG GCCTGGGCTT CGACCGCGCC   1260

GCCCGGCAGG TCCACGAGAA GGCCCTGTTC CTGGTGTTTG CCGCACCAA GAAACGGGAC    1320

CTGTTCTTTA ATGAGATTAA GGCCCGCTCT GGCCAGGACG ATAAGACCGT GTATGAGTAC   1380

CTGTTCAGCC AGCGGCGAAA ACGGCGGGCC CCATCGGCCA CTCGCCAGGG CAAGCGACCC   1440

AGCAAGAACC TTAAGGCTCG CTGCAGTCGG AAGGCACTGC ATGTCAACTT CAAGGACATG   1500

GGCTGGGACG ACTGGATCAT CGCACCCCTT GAGTACGAGG CTTTCCACTG CGAGGGGCTG   1560

TGCGAGTTCC CATTGCGCTC CCACCTGGAG CCCACGAATC ATGCAGTCAT CCAGACCCTG   1620

ATGAACTCGA TGGACCCCGA GTCCACACCA CCCACCTGCT GTGTGCCCAC GCGGCTGAGT   1680

CCCATCAGCA TCCTCTTCAT TGACTCTGCC AACAACGTGG TGTATAAGCA GTATGAGGAC   1740

ATGGTCGTGG AGTCGTGTGG CTGCAGGTAG CAGCACTGGC CCTCTGTCTT CCTGGGTGGC   1800

ACATCCCAAG AGCCCCTTCC TGCACTCCTG GAATCACAGA GGGGTCAGGA AGCTGTGGCA   1860

GGAGCATCTA CACAGCTTGG TGAAGGGATT CAATAAGCTT GCTCGCTCTC TGAGTGTGAC   1920

TTGGGCTAAA GGCCCCCTTT TATCCACAAG TTCCCCTGGC TGAGGATTGC TGCCCGTCTG   1980

CTGATGTGAC CAGTGGCAGG CACAGGTCCA GGGAGACAGA CTCTGAATGG GACTGAGTCC   2040

CAGGAAACAG TGCTTTCCGA TGAGACTCAG CCCACCATTT CTCCTCACCT GGGCCTTCTC   2100

AGCCTCTGGA CTCTCCTAAG CACCTCTCAG GAGAGCCACA GGTGCCACTG CCTCCTCAAA   2160

TCACATTTGT GCCTGGTGAC TTCCTGTCCC TGGGACAGTT GAGAAGCTGA CTGGGCAAGA   2220

GTGGGAGAGA AGAGGAGAGG GCTTGGATAG AGTTGAGGAG TGTGAGGCTG TTAGACTGTT   2280

AGATTTAAAT GTATATTGAT GAGATAAAAA GCAAAACTGT GCCTAAAAAA AAAAAAAAA   2340

A                                                                   2341

(2) INFORMATION FOR SEQ ID NO: 12:

(i) SEQUENCE CHARACTERISTICS:
        (A) LENGTH: 1308 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

CGAGCGTCCG CCGAGCTGGG CTCCGCCAAG GGAATGCGAA CGCGCAAGGA AGGAAGGATG    60

CCGCGGGCGC CGAGAGAGAA TGCCACGGCC CGGGAGCCCC TGGATCGCCA GGAGCCCCCG   120

CCGAGGCCGC AGGAGGAGCC CCAGCGGCGG CCGCCACAGC AGCCTGAAGC TCGGGAGCCT   180

CCCGGCAGGG GCCCGCGCTT GGTGCCCCAC GAGTACATGC TGTCAATCTA CAGGACTTAC   240

TCCATCGCCG AGAAGCTGGG CATCAATGCT AGCTTTTTCC AGTCTTCCAA GTCGGCTAAT   300

ACGATCACTA GCTTTGTAGA CAGGGGACTA GACGATCTCT CGCACACTCC TCTCCGGAGA   360

CAGAAGTATT TGTTTGATGT GTCCACGCTC TCAGACAAAG AAGAGCTGGT GGGCGCGGAC   420

GTGCGGCTGT TTCGCCAGGC GCCCGCTGCC CTGGCGCCGC CGGCGGCCGC TCCGCTTGCA   480

GCTCTTCGCC TGCCAGTCGC CCCTGCTGCT GGAAGCGCGG AGCCTGGACC CGCAGGGGCG   540

CCCCGGCCCG GCTGGGAAGT CTTCGACGTG TGGCGGGGCC TGCGCCCCCA GCCCTGGAAG   600

CAGCTGTGCT TGGAGCTTCG GGCCGCGTGG GGCGGCGAGC CGGGCGCCGC GGAGGACGAG   660

GCGCGCACGC CTGGGCCCCA GCAGCCGCCG CCCCCGGACC TGCGGAGTCT GGGCTTCGGC   720
```

```
CGGAGGGTGC GGACCCCCCA GGAGCGCGCC TTGCTCGTCG TGTTCTCCAG GTCCCAGCGC     780

AAGACCCTGT TCGCCGAGAT GCGCGAGCAG CTGGGCTCGG CGACCGAGGT GGTCGGCCCC     840

GGTGGTGGGG CCGAGGGGTC GGGGCCGCCG CCGCCGCCGC CGCCGCCGCC GCCGTCGGGC     900

ACCCCGGACG CTGGGCTCTG GTCGCCCTCG CCTGGCCGGC GGCGGCGCAC GGCCTTCGCC     960

AGCCGCCACG GCAAGCGGCA CGGCAAGAAG TCGAGGCTGC GCTGCAGCAA GAAGCCCCTG    1020

CACGTGAACT TCAAGGAGCT GGGCTGGGAC GACTGGATTA TCGCGCCCCT GGAGTACGAG    1080

GCCTACCACT GCGAGGGCGT GTGCGACTTC CCGCTACGCT CGCACCTGGA GCCCACCGAC    1140

CACGCCATCA TCCAGACGCT GATGAACTCC ATGGACCCCG GCTCCACCCC GCCCAGCTGC    1200

TGCGTGCCCA CCAAATTGAC TCCCATCAGC ATCTTGTACA TCGACGCGGG CAATAATGTG    1260

GTCTACAACG AGTACGAGGA GATGGTGGTG GAGTCGTGCG GCTGCAGG               1308
```

(2) INFORMATION FOR SEQ ID NO: 13:

(i) SEQUENCE CHARACTERISTICS:
        (A) LENGTH: 501 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

```
Met Arg Leu Pro Lys Leu Leu Thr Phe Leu Leu Trp Tyr Leu Ala Trp
 1               5                  10                  15

Leu Asp Leu Glu Phe Ile Cys Thr Val Leu Gly Ala Pro Asp Leu Gly
                20                  25                  30

Gln Arg Pro Gln Gly Ser Arg Pro Gly Leu Ala Lys Ala Glu Ala Lys
            35                  40                  45

Glu Arg Pro Pro Leu Ala Arg Asn Val Phe Arg Pro Gly Gly His Ser
        50                  55                  60

Tyr Gly Gly Gly Ala Thr Asn Ala Asn Ala Arg Ala Lys Gly Gly Thr
 65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Arg Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
130                 135                 140

Leu Leu Lys Lys Ala Arg Glu Pro Gly Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Val Pro Arg
```

```
                         245                 250                 255
Ser Arg Arg Ala Ala Gln Leu Lys Leu Ser Ser Cys Pro Ser Gly Arg
                260                 265                 270

Gln Pro Ala Ala Leu Leu Asp Val Arg Ser Val Pro Gly Leu Asp Gly
            275                 280                 285

Ser Gly Trp Glu Val Phe Asp Ile Trp Lys Leu Phe Arg Asn Phe Lys
        290                 295                 300

Asn Ser Ala Gln Leu Cys Leu Glu Leu Glu Ala Trp Glu Arg Gly Arg
305                 310                 315                 320

Thr Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Ser
370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe Gly Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
        450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

(2) INFORMATION FOR SEQ ID NO: 14:

(i) SEQUENCE CHARACTERISTICS:
        (A) LENGTH: 436 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Arg Ala Ser Ala Glu Leu Gly Ser Ala Lys Gly Met Arg Thr Arg Lys
1                5                  10                  15

Glu Gly Arg Met Pro Arg Ala Pro Arg Glu Asn Ala Thr Ala Arg Glu
            20                  25                  30

Pro Leu Asp Arg Gln Glu Pro Pro Arg Pro Gln Glu Pro Gln
        35                  40                  45

Arg Arg Pro Pro Gln Gln Pro Glu Ala Arg Glu Pro Pro Gly Arg Gly
50                  55                  60

Pro Arg Leu Val Pro His Glu Tyr Met Leu Ser Ile Tyr Arg Thr Tyr
65                  70                  75                  80

Ser Ile Ala Glu Lys Leu Gly Ile Asn Ala Ser Phe Phe Gln Ser Ser
```

```
                    85                  90                  95
Lys Ser Ala Asn Thr Ile Thr Ser Phe Val Asp Arg Gly Leu Asp Asp
                100                 105                 110
Leu Ser His Thr Pro Leu Arg Arg Gln Lys Tyr Leu Phe Asp Val Ser
                115                 120                 125
Thr Leu Ser Asp Lys Glu Glu Leu Val Gly Ala Asp Val Arg Leu Phe
            130                 135                 140
Arg Gln Ala Pro Ala Ala Leu Ala Pro Ala Ala Pro Leu Ala
145                 150                 155                 160
Ala Leu Arg Leu Pro Val Ala Pro Ala Gly Ser Ala Glu Pro Gly
                165                 170                 175
Pro Ala Gly Ala Pro Arg Pro Gly Trp Glu Val Phe Asp Val Trp Arg
                180                 185                 190
Gly Leu Arg Pro Gln Pro Trp Lys Gln Leu Cys Leu Glu Leu Arg Ala
                195                 200                 205
Ala Trp Gly Gly Glu Pro Gly Ala Ala Glu Asp Glu Ala Arg Thr Pro
            210                 215                 220
Gly Pro Gln Gln Pro Pro Pro Asp Leu Arg Ser Leu Gly Phe Gly
225                 230                 235                 240
Arg Arg Val Arg Thr Pro Gln Glu Arg Ala Leu Leu Val Phe Ser
                245                 250                 255
Arg Ser Gln Arg Lys Thr Leu Phe Ala Glu Met Arg Glu Gln Leu Gly
                260                 265                 270
Ser Ala Thr Glu Val Val Gly Pro Gly Gly Ala Glu Gly Ser Gly
            275                 280                 285
Pro Pro Pro Pro Pro Pro Pro Pro Ser Gly Thr Pro Asp Ala
290                 295                 300
Gly Leu Trp Ser Pro Ser Pro Gly Arg Arg Arg Thr Ala Phe Ala
305                 310                 315                 320
Ser Arg His Gly Lys Arg His Gly Lys Lys Ser Arg Leu Arg Cys Ser
                325                 330                 335
Lys Lys Pro Leu His Val Asn Phe Lys Glu Leu Gly Trp Asp Asp Trp
                340                 345                 350
Ile Ile Ala Pro Leu Glu Tyr Glu Ala Tyr His Cys Glu Gly Val Cys
                355                 360                 365
Asp Phe Pro Leu Arg Ser His Leu Glu Pro Thr Asn His Ala Ile Ile
            370                 375                 380
Gln Thr Leu Met Asn Ser Met Asp Pro Gly Ser Thr Pro Pro Ser Cys
385                 390                 395                 400
Cys Val Pro Thr Lys Leu Thr Pro Ile Ser Ile Leu Tyr Ile Asp Ala
                405                 410                 415
Gly Asn Asn Val Val Tyr Asn Glu Tyr Glu Met Val Val Glu Ser
                420                 425                 430
Cys Gly Cys Arg
            435

(2) INFORMATION FOR SEQ ID NO: 15:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide
```

(ix) FEATURE:
            (A) NAME/KEY: Other
            (B) LOCATION: 3...3
            (D) OTHER INFORMATION: Xaa = I or M or V (xi) SEQUENCE DESCRIPTION: SEQ ID NO: 15:

Trp Ile Xaa Ala Pro Leu Xaa Tyr Glu Ala Xaa His Cys Glu Gly Xaa
1               5                   10                  15

Cys Xaa Phe Pro Leu Arg Ser His Leu Glu Pro Thr Asn His Ala
        20                  25                  30

(2) INFORMATION FOR SEQ ID NO: 16:

(i) SEQUENCE CHARACTERISTICS:
            (A) LENGTH: 31 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 16:

Trp Ile Ile Ala Pro Leu Glu Tyr Glu Ala His His Cys Ala Gly Val
1               5                   10                  15

Cys Asp Phe Pro Leu Arg Ser His Leu Glu Pro Thr Asn His Ala
        20                  25                  30

(2) INFORMATION FOR SEQ ID NO: 17:

(i) SEQUENCE CHARACTERISTICS:
            (A) LENGTH: 31 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 17:

Trp Ile Ile Ala Pro Leu Glu Tyr Glu Ala Phe His Cys Glu Gly Asp
1               5                   10                  15

Cys Glu Phe Pro Leu Arg Ser His Leu Glu Pro Thr Asn His Ala
        20                  25                  30

(2) INFORMATION FOR SEQ ID NO: 18:

(i) SEQUENCE CHARACTERISTICS:
            (A) LENGTH: 31 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 18:

Trp Ile Ile Ala Pro Leu Glu Tyr Glu Ala Tyr His Cys Glu Gly Asp
1               5                   10                  15

Cys Glu Phe Pro Leu Arg Ser His Leu Glu Pro Thr Asn His Ala
        20                  25                  30

(2) INFORMATION FOR SEQ ID NO: 19:

(i) SEQUENCE CHARACTERISTICS:
            (A) LENGTH: 31 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 19:

Trp Ile Val Ala Pro Leu Asp Tyr Glu Ala Tyr His Cys Glu Gly Val
 1               5                  10                  15

Cys Asp Phe Pro Leu Arg Ser His Leu Glu Pro Thr Asn His Ala
            20                  25                  30

(2) INFORMATION FOR SEQ ID NO: 20:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Trp Ile Ile Ala Pro Leu Glu Tyr Glu Ala Tyr His Cys Glu Gly Val
 1               5                  10                  15

Cys Asp Phe Pro Leu Arg Ser His Leu Glu Pro Thr Asn His Ala
            20                  25                  30

(2) INFORMATION FOR SEQ ID NO: 21:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Trp Ile Ile Ala Pro Leu Glu Tyr Glu Ala Tyr His Cys Glu Gly Val
 1               5                  10                  15

Cys Asp Phe Pro Leu Arg Ser His Leu Glu Pro Thr Asn His Ala
            20                  25                  30

(2) INFORMATION FOR SEQ ID NO: 22:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Trp Ile Ile Ala Pro Leu Glu Tyr Glu Ala Tyr His Cys Glu Gly Val
 1               5                  10                  15

Cys Asp Phe Pro Leu Arg Ser His Leu Glu Pro Thr Asn His Ala
            20                  25                  30

(2) INFORMATION FOR SEQ ID NO: 23:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

```
Trp Ile Met Ala Pro Leu Asp Tyr Glu Ala Tyr His Cys Glu Gly Asp
1               5                   10                  15

Cys Asp Phe Pro Leu Arg Ser His Leu Glu Pro Thr Asn His Ala
            20                  25                  30

(2) INFORMATION FOR SEQ ID NO: 24:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Trp Ile Ile Ala Pro Leu Glu Tyr Glu Ala Tyr His Cys Glu Gly Val
1               5                   10                  15

Cys Asp Phe Pro Leu Arg Ser His Leu Glu Pro Thr Asn His Ala
            20                  25                  30
```